(12) United States Patent
Rosen et al.

(10) Patent No.: US 6,251,648 B1
(45) Date of Patent: Jun. 26, 2001

(54) GENE ENCODING HUMAN DNASE

(75) Inventors: Craig Rosen, Laytonsville; Steven M. Ruben, Olney; Mark D. Adams, North Potomac, all of MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/054,989

(22) Filed: Apr. 3, 1998

Related U.S. Application Data

(62) Division of application No. 08/468,012, filed as application No. PCT/US94/04954 on May 5, 1994, now Pat. No. 5,830,744.

(51) Int. Cl.⁷ .............................. C12N 9/22; A61K 38/00
(52) U.S. Cl. ........................ 435/199; 530/300; 530/324
(58) Field of Search .............................. 435/199; 530/300, 530/324

(56) References Cited

U.S. PATENT DOCUMENTS 5,830,744 * 11/1998 Rosen et al. ...................... 435/252.3

FOREIGN PATENT DOCUMENTS

| WO 96/41887 | 12/1996 | (DE) . |
| 19 52 1046C | 12/1998 | (DE) . |
| WO 93/25670 | 12/1993 | (WO) . |

OTHER PUBLICATIONS

Pergolizzi, et al., *Gene,* vol. 168, pp. 267–270 (1996).
Parrish, et al., *Human Molecular Genetics,* 4(9): 1557–1564 (1995).
Aitken et al. (1992) JAMA 267:1947–1951.
Ramsey et al. (1993) Am. Rev. Respir. Dis. 148:145–151.
Shak et al. (1990) PNAS 87:9188–9192,
Yasuda et al. (1990) J. Biochem. 108:393–398.

* cited by examiner

*Primary Examiner*—Einar Stole
(74) *Attorney, Agent, or Firm*—Human Genome Sciences, Inc.

(57) ABSTRACT

A human DNase polypeptide and DNA (RNA) encoding such polypeptide and a procedure for producing such polypeptide by recombinant techniques is disclosed. Also disclosed are methods for utilizing such polypeptide for preventing and/or treating bronchopulmonary conditions. Diagnostic assays for identifying mutations in nucleic acid sequence encoding a polypeptide of the present invention and for detecting altered levels of the polypeptide of the present invention are also disclosed.

51 Claims, 7 Drawing Sheets

FIG. 1A

```
AGCCATGCACTACCCAACTGCACTCCCTCTTCCTCATCCTGGCCAATGGGACCCAGACCTTTCGCATCTGC
 A  M  H  Y  P  T  A  L  L  F  L  I  L  A  N  G  T  Q  T  F  R  I  C
                                                                        70

GCCTTCAATGCCCAGCGGCTGACACTGCCCAAGGTGGCCAGGGAGCAGGTGATGGACACCTTAGTTCGGA
 A  F  N  A  Q  R  L  T  L  P  K  V  A  R  E  Q  V  M  D  T  L  V  R
                                                                        140

TACTGGCTCGCTGTGACATCATGGTGCTGCAGGAGGTGGTGGACTCTTCCGGCAGGCCATCCCGCTCCT
 I  L  A  R  C  D  I  M  V  L  Q  E  V  V  D  S  S  G  S  A  I  P  L  L
                                                                        210

GCTTCGAGAACTCAATCGATTTGATGGCTCTGGGCCCTACAGCAGCCCTGAGCAGCCCCAGCTGGGGCGC
 L  R  E  L  N  R  F  D  G  S  G  P  Y  S  S  P  E  Q  P  Q  L  G  R
                                                                        280
```

(L R E L N R F D G S G P Y S T L S S P Q L G R)

```
AGCACCTACATGGAGACGTATGTGTACTTCTATCGGTCACACAAAACACAGTTCCTGAGTTCCTACGTGT
 S  T  Y  M  E  T  Y  V  Y  F  Y  R  S  H  K  T  Q  V  L  S  S  Y  V
                                                                        350
```

FIG. 1B

```
ACAACGATGAGGATGACGTCTTTGCCCGGGAGCCATTTGTGGCCCAGTTCTCTTTGCCCAGCAATGTCCT    420
 Y  N  D  E  D  D  V  F  A  R  E  P  F  V  A  Q  F  S  L  P  S  N  V  L

TCCCAGCCTGTGTTGGTCCCGCTGCACACCACTCCTAAGGCCGTAGAGAAGGAGCTGAACGCCCTCTAC    490
 P  S  L  V  L  V  P  L  H  T  T  P  K  A  V  E  K  E  L  N  A  L  Y

GATGTGTTTCTGGAGGTCTCCCAGCACTGGCAGAGCAAGGACGTGATCCTGCTTGGGGACTTCAATGCTG    560
 D  V  F  L  E  V  S  Q  H  W  Q  S  K  D  V  I  L  L  G  D  F  N  A

ACTGCGCTTCACTGACCAAAAAGCGCCTTGACAAGCTGGAGCTGCGGACTGAGCCAGGCTTCCACTGGGT    630
 D  C  A  S  L  T  K  K  R  L  D  K  L  E  L  R  T  E  P  G  F  H  W  V

GATTGCCGATGGGGAGGACACCACAGTGCGCCAGCACCACTGCACCTATGACCGGGTCGTGCTGCAC    700
 I  A  D  G  E  D  T  T  V  R  A  S  T  H  C  T  Y  D  R  V  V  L  H
```

FIG. 1C

```
GGGGAGCGCTGCCGGAGTCTGCTGCACACTGCGGGCTGCCTTGACTTCCCCACGAGCTTCCAGCTCACCG  770
 G  E  R  C  R  S  L  L  H  T  A  A  A  F  D  F  P  T  S  F  Q  L  T

AGGAGGAGGCCCTCAACATCAGTGACCACTACCCCGTGGAGGTGGAGCTGAAGCTGAGCCAGGCGCACAG  840
 E  E  E  A  L  N  I  S  D  H  Y  P  V  E  V  E  L  K  L  S  Q  A  H  S

CGTCCAGCCTCTCAGCCTCACTGTTCTGTTCCTGCTATCACTCCCTGTCCCTCAGCTGTGCCCTGCTGCC  910
 V  Q  P  L  S  L  T  V  L  L  L  L  S  L  L  S  P  Q  L  C  P  A  A

TGAGCGTCCCCCTACCCCCCCAGGGCCTTGCTGCCTTTTGGGACTTAAACCCAGCCTCCCCGTCCATCC  980
 .  A  S  P  Y  P  P  R  A  C  C  L  L  G  L  K  P  Q  P  P  S  I

AGCCCTGGGGCTGGGGGGCTTCAACTATAGTGCCCTGTGACTGTAGTCCACCCCTGCCTGCTTGTTG   1050
 Q  P  W  G  W  G  A  S  T  I  V  A  L  .  S  T  P  A  C  L  V  .

ATTTG
↑ 1055
F ↑
```

PURIFICATION OF DNase lane 1, cell extract  lane 4, pH 6.0
lane 2, flow through  lane 5, pH 5.0
lane 3, pH 8.0 wash  lane 6, pH 2.0

DEGRADATION OF SUPERCOILED DNA ul DNase    bl   0   5   10   20 bl-bluescript control

GENE ENCODING HUMAN DNASE

This application is a Divisional Application entitled to priority benefits under 35 U.S.C §120 for the information set forth in Ser. No. 08/468,012, filed Jun. 6, 1995 which is a Continuation-In-Part of PCT/US94/04954, filed May 5, 1994.

This invention relates to newly identified polynucleotide sequences, polypeptides encoded by such sequences, the use of such polynucleotides and polypeptides, as well as the production of such polynucleotides and polypeptides. More particularly, the polypeptide of the present invention is a human deoxyribonuclease (DNase). The invention also relates to inhibiting the action of such polypeptide.

DNase is a phosphodiesterase capable of hydrolyzing polydeoxyribonucleic acid. It acts to extensively and nonspecifically degrade DNA and in this regard it is distinguished from the relatively limited and sequence-specific restriction endonucleases. The degradation activity as stated above is non-specific. However, it also degrades double stranded DNA to yield 5'-oligonucleotides. There are two types of DNase, both DNase I and II. DNase I has a pH optimum near neutrality, an obligatory requirement for divalent cations, and produces 5'-phosphate nucleotides on hydrolysis of DNA. DNase II exhibits an acid pH optimum, can be activated by divalent cations and produces 3'-phosphate nucleotides on hydrolysis of DNA. Multiple molecular forms of DNase I and II also are known.

The DNase I is mainly a digestive enzyme, however, activities similar to DNase I had been found in other tissues suggesting that it may have other functions (Laskowski, ref. 1971). For example, it has been suggested that DNase may play a role in the polymerization of actin. (Suck, et al., ref. 1981). DNase's in prokaryotic cells participate in a variety of metabolic functions, including genetic recombination, repair of DNA damage, restriction of foreign DNA and transport of DNA into cells.

DNase from various species have been purified to a varying degree. Bovine DNase A, B, C, and D was purified and completely sequenced as early as 1973 (Liao et al., *J. Biol. Chem.* 248:1489 [1973]). Porcine and bovine DNase have been purified and fully sequenced (Paudel et al., *J. Biol. Chem.* 261:16006 [1986]). Human urinary DNase was reported to have been purified to an electrophoretically homogenous state and the N-terminal amino acid observed to be leucine; no other sequence was reported (Ito et al., *J. Biol. Chem.* 95:1399 [1984]).

Recently, the bovine and human DNase I genes have been cloned and expressed, as shown in PCT international application number PCT/US89/05744, applied for by Genentech, Inc., which discloses human DNase isolated from the pancreas.

The Shields et al. reference described the expression cloning of part of the gene for bovine DNase I and expression of a fusion product in *E. coli* which was biologically and immunologically active (*Biochem. Soc. Trans.* 16:195 [1988]). The DNase product of Shields et al., however, was toxic to the host cells and could only be obtained by the use of an inducible promoter. Furthermore, great difficulty was encountered in attempts to isolate plasmid DNA from either clone, an obstacle attributed to constitutive levels of expression of DNase from the clones, so that these authors were unable to determine the sequence for the DNase-encoding nucleic acid. According to Shields et al., the inability to recover the plasmid was the result of constitutive expression of DNase even when the promoter was repressed at low temperature. This would create a considerable obstacle since Shields et al. had only identified the clone by expression cloning, which necessarily requires that the DNase be placed under the control of a promoter of some sort.

DNase finds a number of known utilities and has been used for therapeutic purposes. Its principal therapeutic use has been to reduce the viscosity of pulmonary secretions in such diseases as pneumonia, cystic fibrosis, thereby aiding in the clearing of respiratory airways. Obstruction of airways by secretions can cause respiratory distress, and in some cases, can lead to respiratory failure and death.

In accordance with one aspect of the present invention, there is provided a novel mature polypeptide, as well as biologically active and diagnostically or therapeutically useful fragments, analogs and derivatives thereof. The polypeptide of the present invention is of human origin.

In accordance with another aspect of the present invention, there are provided isolated nucleic acid molecules encoding a polypeptide of the present invention including mRNAs, DNAs, cDNAs, genomic DNAs as well as analogs and biologically active and diagnostically or therapeutically useful fragments thereof.

In accordance with yet a further aspect of the present invention, there is provided a process for producing such polypeptide by recombinant techniques comprising culturing recombinant prokaryotic and/or eukaryotic host cells, containing a nucleic acid sequence encoding a polypeptide of the present invention, under conditions promoting expression of said protein and subsequent recovery of said protein.

In accordance with yet a further aspect of the present invention, there is provided a process for utilizing such polypeptide, or polynucleotide encoding such polypeptide for therapeutic purposes, for example, for the enzymatic alteration of the viscosity of bronchopulmonary secretions.

In accordance with yet a further aspect of the present invention, there are provided antibodies against such polypeptides.

In accordance with yet a further aspect of the present invention, there is also provided nucleic acid probes comprising nucleic acid molecules of sufficient length to specifically hybridize to a nucleic acid sequence of the present invention.

In accordance with still another aspect of the present invention, there are provided diagnostic assays for detecting diseases or susceptibility to diseases related to mutations in the nucleic acid sequences encoding a polypeptide of the present invention.

In accordance with yet a further aspect of the present invention, there is provided a process for utilizing such polypeptides, or polynucleotides encoding such polypeptides, for in vitro purposes related to scientific research, for example, synthesis of DNA and manufacture of DNA vectors.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A–1C, collectively, show the cDNA and corresponding deduced amino acid sequence of the polypeptide of the present invention. The amino acids are represented by their standard one letter abbreviations. The protein shown is the preprocessed form of the protein.

Figure 2:
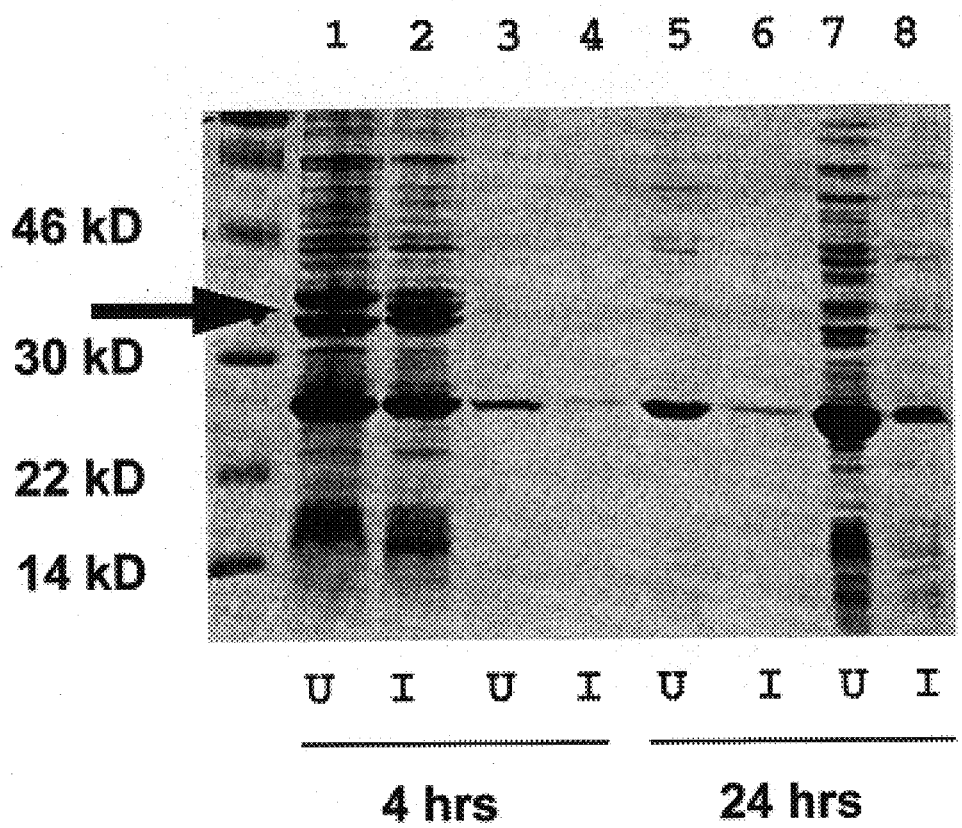
FIG. 2 illustrates the amount of DNase released from the pelleted fraction of a bacterial expression system as opposed to the soluble fraction at different time intervals.

In accordance with one aspect of the present invention, there is provided a DNA sequence (and corresponding RNA sequence) as set forth in FIG. 1 of the drawings and/or DNA (RNA) sequences encoding the same polypeptide as the sequence of FIGS. 1A–1C, collectively of the drawings, as well as fragment portions, derivatives, analogs and all allelic variants of such sequences. The polypeptide of FIGS. 1A–1C, collectively is the preprocessed form of the protein and has a leader sequence. The processed or mature form begins at amino acid 19.

In accordance with another aspect of the present invention, there is provided a polynucleotide which encodes the same polypeptide as the polynucleotide of the cDNA clone deposited as ATCC deposit number 75515, deposited on Aug. 4, 1993, and/or fragments, analogs, derivatives or allelic variants of such polynucleotide.

The ATCC number referred to above is directed to a biological deposit with the ATCC, 10801 University Boulevard, Manses, Va. 20110-2209. Since the strain referred to is being maintained under the terms of the Budapest Treaty, it will be made available to a patent office signatory to the Budapest Treaty.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A–1C, collectively (SEQ ID NO:1) or that of the deposited clone or may be a different coding sequence which coding sequence, as a result of the redundancy or degeneracy of the genetic code, encodes the same mature polypeptide as the DNA of FIGS. 1A–1C, collectively (SEQ ID NO:1) or the deposited cDNA.

The polynucleotide which encodes for the mature polypeptide of FIGS. 1A–1C, collectively (SEQ ID NO:2) or for the mature polypeptide encoded by the deposited cDNA may include, but is not limited to: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1A–1C, collectively (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides, encoding the same mature polypeptide as shown in FIGS. 1A–1C, collectively (SEQ ID NO:2) or the same mature polypeptide encoded by the cDNA of the deposited clone as well as variants of such polynucleotides which variants encode for a fragment, derivative or analog of the polypeptide of FIGS. 1A–1C, collectively (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIGS. 1A–1C, collectively (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95 identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1A–1C, collectively (SEQ ID NO:1) or the deposited cDNA (s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90t and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a polypeptide which has the deduced amino acid sequence of FIGS. 1A–1C, collectively (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIGS. 1A–1C, collectively (SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIGS. 1A–1C, collectively (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.\ coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.\ coli.$ The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as $E.\ coli,$ Streptomyces, $Salmonella\ typhimurium;$ fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, $pD_{10}$, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of $E.\ coli$ and $S.\ cerevisiae$ TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purifications Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

Purified DNase of the present invention may be employed to enzymatically reduce the viscosity of mucus in the manner as described above. Based on this activity it would be of particular use for the treatment of patients with pulmonary disease who have abnormal or viscous or inspissated purulent secretions in conditions such as acute or chronic bronchial pulmonary disease (infectious pneumonia, bronchitis, or tracheobronchitis, bronchiectasis, cystic fibrosis, asthma, TB, or fungal infections), atelectasis due to tracheal or bronchial impaction and complications due to tracheostomy. For such therapies, a solution or finely divided dry preparation of human DNase is instilled in conventional fashion into the bronchi, e.g., by aerosolization of a solution of DNase.

In addition to these direct uses, DNase would have adjunctive treatment for the management of abscesses of closed spaced infections, emphysema, meningitis, peritonitis, sinusitis, otitis, periodontitis, pancreatitis, cholelithiasis, endocroditis, and septic arthritis, as well as in topical treatments in a variety of inflammatory and infected lesions, such as infected lesions of the skin and/or mucosal membranes, surgical wounds, ulcerative lesions and burns.

Human DNase finds utility in maintaining the flow in medical conduits communicating with a body cavity, including surgical drainage tubes, urinary catheters, peritoneal dialysis ports, and intratracheal oxygen catheters.

The DNase of the present invention may also improve the efficacy of antibiotics in infections. The DNase may also be useful in degrading DNA contaminants in pharmaceutical preparations. Finally, DNase may be useful in treating non-infected conditions in which there is an accumulation of cellular debris, including cellular DNA. For example, DNase will be useful after systemic administration in the treatment of pyelonephritis and tubulo-interstitial kidney disease.

The polynucleotides and polypeptides of the present invention may be employed as research reagents and materials for discovery of treatments and diagnostics to human disease.

The polypeptides of the present invention may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

The pharmaceutical compositions may be administered in a convenient manner such as by the oral, topical, parenterally, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art and are apparent from the teachings herein. For example, cells may be engineered by the use of a retroviral plasmid vector containing RNA encoding a polypeptide of the present invention.

Similarly, cells may be engineered in vivo for expression of a polypeptide in vivo by, for example, procedures known in the art. For example, a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the gene of the present invention as a diagnostic. Detection of a mutated form of the gene will allow a diagnosis of a disease or a susceptibility to a disease which results from underexpression of Human DNase.

Individuals carrying mutations in the gene of the present invention may be detected at the DNA level by a variety of techniques. Nucleic acids for diagnosis may be obtained from a patient's cells, including but not limited to blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding Human DNase can be used to identify and analyze mutations. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions -according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of the polypeptide of the present invention in various tissues since an over-expression of the proteins compared to normal control tissue samples can detect the presence of Human DNase. Assays used to detect levels of the polypeptide of the present invention in a sample derived from a host are well-known to those of skill in the art and include radioimmunoassays, competitive-binding assays, Western Blot analysis and preferably an ELISA assay. An ELISA assay initially comprises preparing an antibody specific to the DNase antigen, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attached to any of the polypeptide of the present invention attached to the polystyrene dish. All unbound monoclonal antibody is washed out with buffer. The reporter antibody linked to horseradish peroxidase is now placed in the dish resulting in binding of the reporter antibody to any monoclonal antibody bound to the polypeptide of the present invention. Unattached reporter antibody is then washed out. Peroxidase substrates are then added to the dish and the amount of color developed in a given time period is a measurement of the amount of the polypeptide of the present invention present in a given volume of patient sample when compared against a standard curve.

A competition assay may be employed wherein antibodies specific to the polypeptide of the present invention are attached to a solid support and labeled DNase and a sample derived from the host are passed over the solid support and the amount of label detected attached to the solid support can be correlated to a quantity of the polypeptide of the present invention in the sample.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA having at least 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour or longer at 37° C. are ordinarily used, but may vary in accordance with the supplier's instructions. After digestion the reaction is electrophoresed directly on an agarose gel to isolate the desired fragment.

Size separation of the cleaved fragments is performed using a 0.8–2.0 percent polyagarose gel. (Maniatis)

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

EXAMPLE 1

Bacterial Expression and Purification of Human DNase

The DNA sequence encoding for human DNase, pBL-SKDNase (ATCC # 75515) is initially amplified using PCR oligonucleotide primers corresponding to the 5' and 3' end of the DNA sequence to synthesize insertion fragments. The 5' oligonucleotide primer has the sequence GACGCCGGATCCCACTACCCAACTGCA, (SEQ ID NO:3) contains a BamHI restriction enzyme site followed by 15 nucleotides of DNase coding sequence following the initiation codon; the 3' sequence 5'-GGCTGCTCTAGACAGCGTAGTCTGGCAGGT CGTATGGGTACTTCAGCTCCACCTCCACGGGGTAG-3' (SEQ ID NO:4) contains complementary sequences to XbaI site and is in the 3' untranslated region of the gene. The restriction enzyme sites correspond to the restriction enzyme sites on the bacterial expression vector pQE-9. (Qiagen, Inc. 9259 Eton Avenue, Chatsworth, Calif., 91311) The plasmid vector encodes antibiotic resistance (Amp$^r$), a bacterial origin of replication (ori), an IPTG-regulatable promoter/operator (P/O), a ribosome binding site (RBS), a 6-histidine tag (6-His) and restriction enzyme cloning sites. The pQE-9 vector was digested with BamHI and XbaI and the insertion fragments were then ligated into the pQE-9 vector maintaining the reading frame initiated at the bacterial RBS. FIG. 7 shows a schematic representation of this arrangement. The ligation mixture was then used to transform the E. coli strain available from Qiagen under the trademark m15/rep4. M15/rep4 contains multiple copies of the plasmid pREP4, which expresses the lacI repressor and also confers kanamycin resistance (Kan$^r$). Transformants are identified by their ability to grow on LB plates containing both Amp and Kan. Clones containing the desired constructs were grown overnight (O/N) in liquid culture in LB media supplemented with both Amp (100 µg/ml) and Kan (25 µg/ml). The O/N culture is used to inoculate a large culture at a ratio of 1:100 to 1:250. The cells were grown to an optical density at 600 nm (O.D.$^{600}$) between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 2–4 hours. Cells were then harvested by centrifugation. Expression of DNase was tested by solubilizing a portion of the E. coli and analyzing on a SDS polyacrylamide gel. The presence of a new protein corresponding to 33 kd following induction demonstrated expression of the DNase. (FIG. 2).

Figure 3:
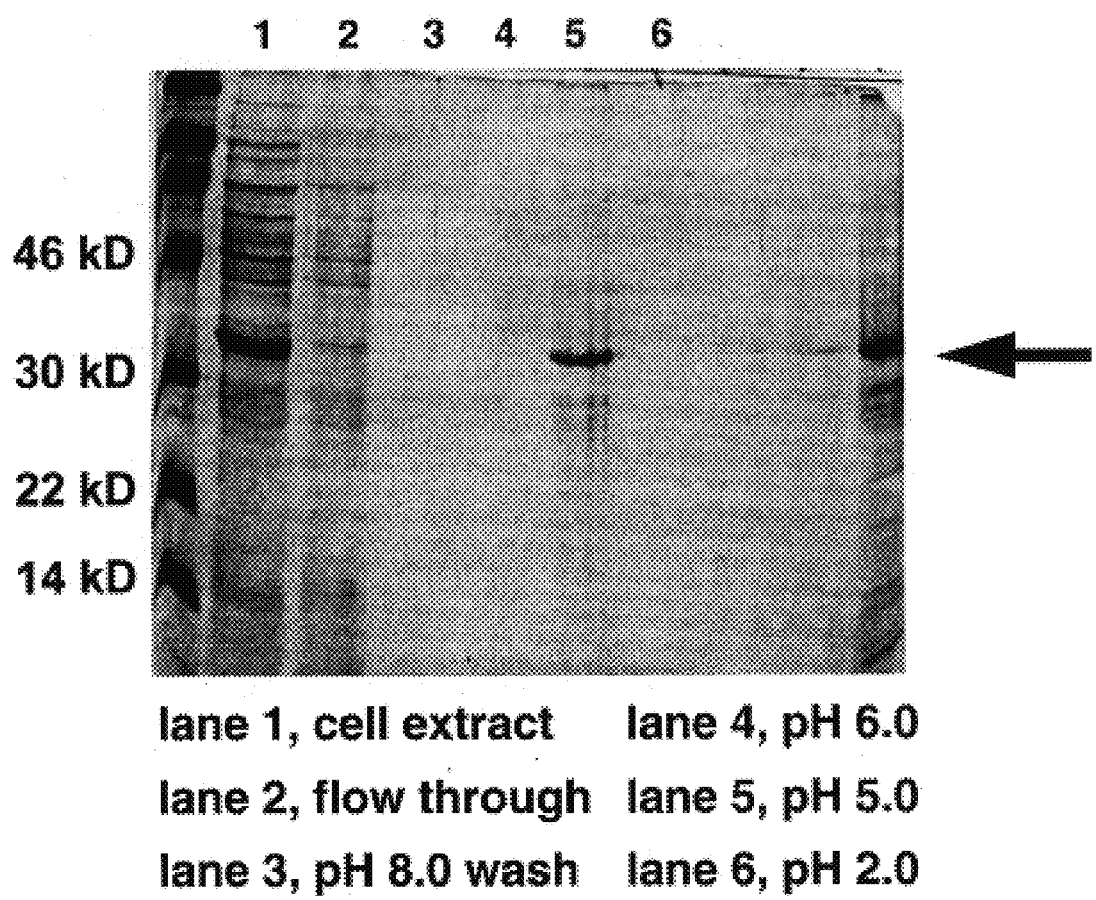
FIG. 3 shows the rate of success of purification of DNase in different mediums and at different pHs.

Purification of protein was accomplished by utilization of the hexa-histidine sequence added to the DNase sequence by the pQE-9 vector. Following induction of cells, the E. coli pellet was solubilized in 6M guanidine HCL. The DNase was purified using a Nickel-Chelate resin column that has a high affinity for the hexa-histidine tag. (Hachuli, E. et al., Genetic Engineering, Principle and Methods, 12:87–98 Plenum Press, New York (1990). The column was then washed, and the DNase was eluted at a pH of 5. Protein renaturation out of Guanidine HCl can be accomplished by several protocols. (Jaenicke, R. et al. Protein Structure—a practical approach IRL Press, New York (1990). Initially, step dialysis is utilized to remove the GnHCl. Alternatively, the purified protein isolate from the Ni-chelate column can be bound to a second column over which a decreasing linear GnHCl gradient is run. The protein is allowed to renature while bound to the column and is subsequently eluted with GnHCl, pH 5.0. Finally, soluble protein is dialyzed against a storage buffer containing 140 mM NaCl, 20 mM $NaPO_4$ and 10% w/v Glyconol. The purified protein was analyzed by SDS-PAGE. (FIG. 3).

EXAMPLE 2
Expression of DNase in COS Cells

The expression of plasmid, soCMVDNase HA is derived from a vector SoCMVIN/Amp containing: 1) SV40 origin of replication, β globin intron, 2) ampicillin resistance gene, 3) *E. coli* replication origin, 4) CMV promoter followed by a polylinker region, a SV40 intron and polyadenalytion site. (Ruben, S., et. al. *Molecular and Cellular Biology*, 444–454 (1992). A DNA fragment encoding the entire DNase and a HA tag fused in frame to its 3' end was cloned into the polylinker region of the vector, therefore, the recombinant protein expression is directed under the CMV promoter. The HA tag corresponds to an epitope derived from the influenza hemagglutinin protein (MYPYDVPDYA), (SEQ ID NO:5) as previously described (I. Wilson, et al. *Cell*, 37:767 (1984). The infusion of HA tag to our target protein allows easy detection of the recombinant protein with an antibody that recognizes the HA epitope.

The plasmid construction strategy is described as follow:

The DNA insert was constructed by PCR on the original EST using two primers: the 5' primer GACGCCGGATCCCACTACCCAACTGCA (SEQ ID NO:3) contains a BamHI site followed by 15 nucleotides of DNase coding sequence starting from the initiation codon; the 3' sequence GGCTGCTCTAGACAGCGTAGTCTGGCAGGTCGTATGGGTACTTCAGCTCCACCTCCACGGGGTAG (SEQ ID NO:4) contains complementary sequences to the XBaI site, translation stop codon, HA tag and the 23 nucleotides of the DNase coding sequence (not including the stop codon) that correspond to pancreatic DNase terminal residues. Therefore, the PCR product contains a BamHI site, DNase coding sequence, HA tag fused in frame, followed by a translation termination stop codon next to the HA tag, and a XbaI site. The PCR amplified DNA fragment and the vector, SoCMVIN/amp, were digested with BamHI and XbaI restriction enzyme and ligated. The ligation mixture was transformed into *E. coli* strain available under the trademark SURE. The transformed culture was plated on ampicillin media plates and resistant colonies were selected. Plasmid DNA was isolated from transformants and examined by restriction analysis for the presence of the correct fragment. For expression of the recombinant DNase, COS cells were transfected with the expression vector by DEAE-DEXTRAN method. (J. Sambrook, E. Fritsch, T. Maniatis, *Molecular Cloning: A Laboratory Manual*, Cold Spring Laboratory Press, 1989.) The expression of the DNase-HA protein was detected by radiolabelling and immunoprecipitation method. Cells were labelled for 8 hours with $^{35}$S-cysteine two days post transfection. (E. Harlow, D. Lane, *Antibodies: A Laboratory manual*, Cold Spring Harbor Laboratory Press, (1988)). Culture media were then collected and cells were lysed with detergent. (RIPA buffer (150 mM NaCL, 1% NP-40, 0.1% SDS, 1% NP-40, 0.5% DOC, 50 mM Tris, pH7.5). (I. Wilson et al. Id. 37:767 (1984)). Both cell lysate and culture media were precipitated with a HA specific monoclonal antibody. Proteins precipitated were analyzed on 15% SDS-PAGE gels.

EXAMPLE 3
Tissue Distribution of DNase

Figure 4:
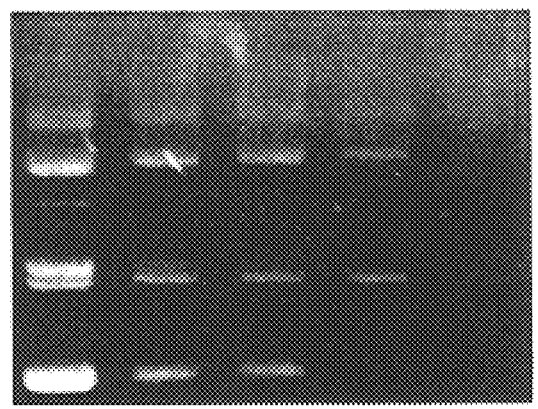
FIG. 4 depicts the ability of DNase to digest double-stranded DNA.

To demonstrate tissue distribution of DNase, Northern blot analysis was performed. Total RNA was prepared from various human tissues and electrophoresed on denaturing agarose gels. The RNA was blotted onto nylon membranes and probed with a DNase cDNA probe corresponding to the EcoRI-Xho fragment of pBLSKDNase prepared by random priming. Exposure of the blot to film revealed that DNase is most abundant in tissue from the heart and lungs with some expression in the spleen. (FIG. 4). Total cellular RNA samples were isolated with RNAzol™ B system (Biotecx Laboratories, Inc., 6023 South Loop East, Houston, Tex. 77033.) About 10 ug of total RNA isolated from each human tissue specified was separated on 1% agarose gel and blotted onto a nylon filter (Sambrook, Fritsch, and Maniatis, *Molecular Cloning*, Cold Spring Harbor Press, (1989)). The labeling reaction was done according to the Stratagen Prime-It kit with 50 ng of the Eco RI-XhoI fragment of pBL sle DNase DNA fragment. The labeled DNA was purified with a Seclect-G-50 column. (5 Prime—3 Prime, Inc. 5603 Arapahoe Road, Boulder, Colo. 80303). The filter was then hybridized with radioactive labeled full length thrombin inhibitor gene at 1,000,000 cpm/ml in 0.5 M $NaPO_4$ and 7% SDS overnight at 65° C. After wash twice at room temperature and twice at 60° C. with 0.5×SSC, 0.1% SDS, the filters were then exposed at −70° C. overnight with intensifying screen. (FIG. 4).

EXAMPLE 4
Assays for DNase Activity

Several assays are available to measure DNase Activity. The first assay measures the hydrolysis of $^{32}$P-labeled DNA.

Degradation of $^{32}$P-DNA was prepared using a Random Prime Labeling Kit (Strategene's Prime It II) using $^{32}$P-dCTP, non-radioactive dGTP, dTTP, dATP and Exo (−) Klenow Enzyme. 1 ul of template (25 ng), 10 ul of random oligonucleotide primers and 23 ul of water were mixed and incubated at 100° C. for 5 minutes. 10 ul of 5×dCTP primer buffer, 5 ul of −$^{32}$PdCTP (3.000 Ci/mMole) and 1 ul Exo (−) Klenow Enzyme (5 U/ul) were added to the reaction mixture and incubated at 37° C. for 15 minutes. The free nucleotides were separated from the radiolabled DNA by centrifugation through a Sephadex G-50 column.

DNase activity was then measured by incubating $5×10^5$ cpm $^{32}$P-DNA and 20 ul of protein in DNase buffer (40 mM TRIS-HCl pH 7.6, 50 mM NaCL, 0.1 mM DTT, 6 mM $MgCl_2$, 1 mM $CaCl_2$) in a total volume of 100 ul. 20 ul were removed for time point 0 and for each subsequent time point. TCA precipitable counts were used to determine % activity. (FIG. 6).

To the 20 ul of the DNase assay reaction mixture, 20 ul of 10% TCA was added and mixed. 20 ul was spotted onto a glass filter disk (unincorporated counts). To the remaining 20 ul, an additional 200 ul of 10% TCA was added and then applied to a prewet glass filter disk on a vacuum manifold and the vacuum applied. The disks were washed twice with 3 ml 10% TCA then twice with 3 ml 100% Ethanol and the filter allowed to dry. The filter disks were then place into a liquid scintillation vial containing 3 ml of liquid scintillation cocktail and $^{32}$P counts were measured in a Liquid scintillation counter. Percent incorporation=Incorporated Counts/Unincorporated counts.

Figure 5:
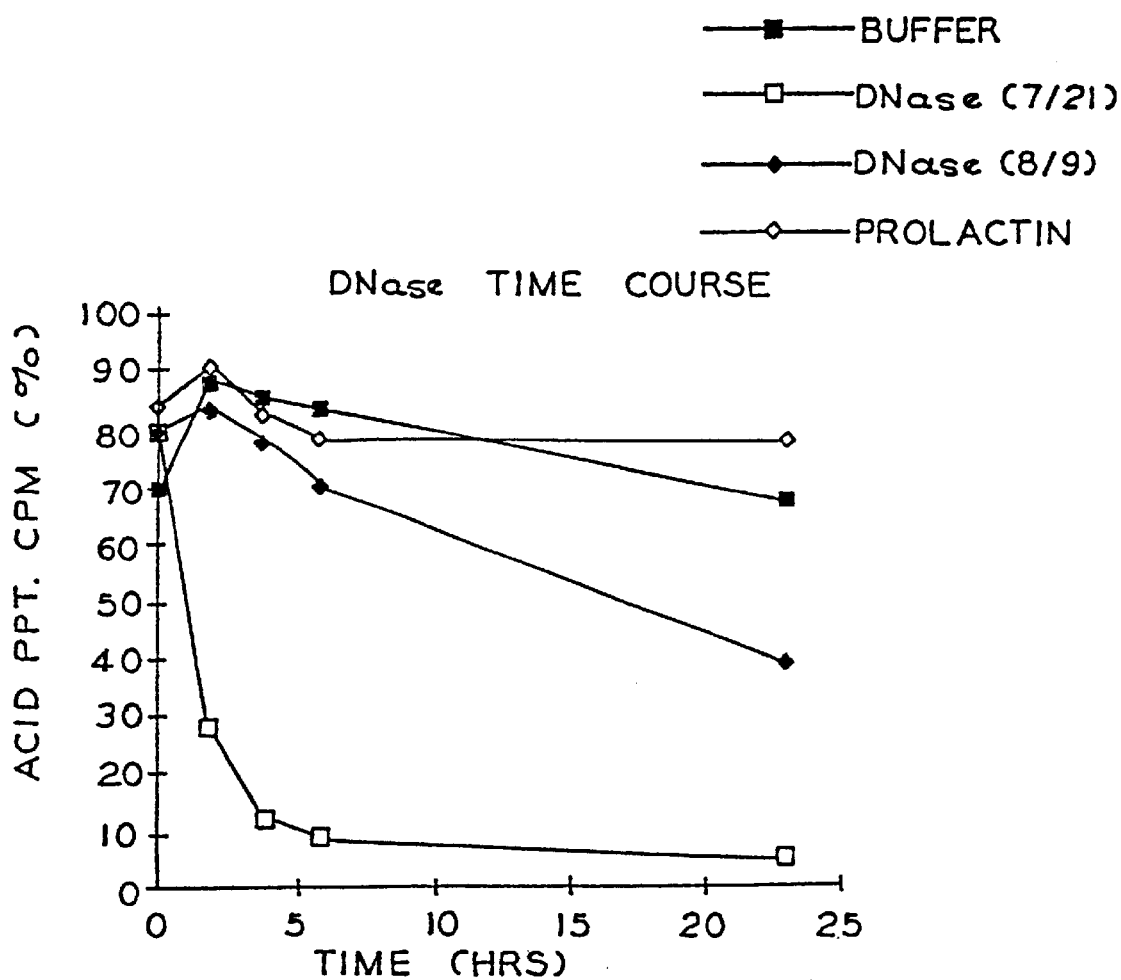
FIG. 5 demonstrates DNase activity. DNA was labeled with $^{32}$P-dCTP. DNase is then incubated with a fixed amount of labeled DNA and samples were removed and counted by liquid scintillation.

A second assay takes advantage of the ability of DNase to nick and digest double-stranded DNA. Supercoiled plasmid DNA is incubated with DNase and samples are removed at time points following addition of the DNase. The samples are electrophoresed on agarose gels and the conversion from supercoiled to relaxed DNA is observed following addition of the DNase. (FIG. 5).

A rapid plate DNase assay can also be used in which test agar contains both DNA and methyl green. Purified protein or supernatants from transfected cells are spotted on the plates along with a standard amount of bovine DNase. DNase activity is measured by visualizing the size of the cleared zone on the plate.

EXAMPLE 5

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10 FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer contains an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated polypeptide, having DNAse activity or capable of inducing antibodies specific for the polypeptide of SEQ ID NO:2, comprising a first amino acid sequence at least 90% identical to a second amino acid sequence selected from the group consisting of:
   (a) amino acids −18 to +279 of SEQ ID NO:2;
   (b) amino acids −17 to +279 of SEQ ID NO:2;
   (c) amino acids −1 to +279 of SEQ ID NO:2;
   (d) a polypeptide encoded by the cDNA contained in ATCC Deposit No.75515;
   (e) a mature polypeptide encoded by the cDNA contained in ATCC Deposit No. 75515;
   (f) at least 30 contiguous amino acids of SEQ ID NO:2; and
   (g) at least 50 contiguous amino acids of SEQ ID NO:2.

2. The isolated polypeptide of claim 1, wherein said first amino acid sequence is at least 90% identical to (a).

3. The isolated polypeptide of claim 2, wherein said first amino acid sequence is at least 95% identical to (a).

4. An isolated polypeptide produced by the method comprising:
   (a) expressing the polypeptide of claim 3 from a host cell; and
   (b) recovering said polypeptide.

5. The isolated polypeptide of claim 3, wherein said first amino acid sequence is (a).

6. An isolated polypeptide produced by the method comprising:
   (a) expressing the polypeptide of claim 5 from a host cell; and
   (b) recovering said polypeptide.

7. The isolated polypeptide of claim 1, wherein said first amino acid sequence is at least 90% identical to (b).

8. The isolated polypeptide of claim 7, wherein said first amino acid sequence is at least 95% identical to (b).

9. An isolated polypeptide produced by the method comprising:
   (a) expressing the polypeptide of claim 8 from a host cell; and
   (b) recovering said polypeptide.

10. The isolated polypeptide of claim 8, wherein said first amino acid sequence is (b).

11. An isolated polypeptide produced by the method comprising:
    (a) expressing the polypeptide of claim 10 from a host cell; and
    (b) recovering said polypeptide.

12. The isolated polypeptide of claim 1, wherein said first amino acid sequence is at least 90% identical to (c).

13. The isolated polypeptide of claim 12, wherein said first amino acid sequence is at least 95% identical to (c).

14. An isolated polypeptide produced by the method comprising:
    (a) expressing the polypeptide of claim 13 from a host cell; and
    (b) recovering said polypeptide.

15. The isolated polypeptide of claim 13, wherein said first amino acid sequence is (c).

16. An isolated polypeptide produced by the method comprising:
    (a) expressing the polypeptide of claim 15 from a host cell; and
    (b) recovering said polypeptide.

17. The isolated polypeptide of claim 1, wherein said first amino acid sequence is at least 90% identical to (d).

18. The isolated polypeptide of claim 17, wherein said first amino acid sequence is at least 95% identical to (d).

19. An isolated polypeptide produced by the method comprising:
    (a) expressing the polypeptide of claim 18 from a host cell; and
    (b) recovering said polypeptide.

20. The isolated polypeptide of claim 18, wherein said first amino acid sequence is (d).

21. An isolated polypeptide produced by the method comprising:
    (a) expressing the polypeptide of claim 20 from a host cell; and
    (b) recovering said polypeptide.

22. The isolated polypeptide of claim 1, wherein said first amino acid sequence is at least 90% identical to (e).

23. The isolated polypeptide of claim 22, wherein said first amino acid sequence is at least 95% identical to (e).

24. An isolated polypeptide produced by the method comprising:
    (a) expressing the polypeptide of claim 23 from a host cell; and
    (b) recovering said polypeptide.

25. The isolated polypeptide of claim 23, wherein said first amino acid sequence is (e).

26. An isolated polypeptide produced by the method comprising:
    (a) expressing the polypeptide of claim 25 from a host cell; and
    (b) recovering said polypeptide.

27. The isolated polypeptide of claim 1, wherein said first amino acid sequence is at least 90% identical to (f).

28. The isolated polypeptide of claim 27, wherein said first amino acid sequence is at least 95% identical to (f).

29. An isolated polypeptide produced by the method comprising:
    (a) expressing the polypeptide of claim 28 from a host cell; and
    (b) recovering said polypeptide.

30. The isolated polypeptide of claim 28, wherein said first amino acid sequence is (f).

31. An isolated polypeptide produced by the method comprising:
    (a) expressing the polypeptide of claim 30 from a host cell; and
    (b) recovering said polypeptide.

32. The isolated polypeptide of claim 1, wherein said first amino acid sequence is at least 90% identical to (g).

33. The isolated polypeptide of claim 32, wherein said first amino acid sequence is at least 95% identical to (g).

34. An isolated polypeptide produced by the method comprising:
    (a) expressing the polypeptide of claim 33 from a host cell; and
    (b) recovering said polypeptide.

35. The isolated polypeptide of claim 33, wherein said first amino acid sequence is (g).

36. An isolated polypeptide produced by the method comprising:
    (a) expressing the polypeptide of claim 35 from a host cell; and
    (b) recovering said polypeptide.

37. The isolated polypeptide of claim 1 further comprising a heterologous polypeptide.

38. A composition comprising the polypeptide of claim 1.

39. An isolated polypeptide, having DNAse activity or capable of inducing antibodies specific for the polypeptide of SEQ ID NO:2, comprising a first amino acid sequence at least 90% identical to a second amino acid sequence selected from the group consisting of:

a) a polypeptide fragment of SEQ ID NO:2 wherein the polypeptide fragment has DNAse activity; and b) a polypeptide fragment of the polypeptide encoded by the cDNA contained in ATCC Deposit No. 75515 wherein the polypeptide fragment has DNAse activity.

40. The isolated polypeptide of claim 39, wherein said first amino acid sequence is at least 90% identical to (a).

41. The isolated polypeptide of claim 40, wherein said first amino acid sequence is at least 95% identical to (a).

42. An isolated polypeptide produced by the method comprising:

(a) expressing the polypeptide of claim 41 from a host cell; and (b) recovering said polypeptide.

43. The isolated polypeptide of claim 41, wherein said first amino acid sequence is (a).

44. An isolated polypeptide produced by the method comprising:

(a) expressing the polypeptide of claim 43 from a host cell; and (b) recovering said polypeptide.

45. The isolated polypeptide of claim 39, wherein said first amino acid sequence is at least 90% identical to (b).

46. The isolated polypeptide of claim 45, wherein said first amino acid sequence is at least 95% identical to (b).

47. An isolated polypeptide produced by the method comprising:

(a) expressing the polypeptide of claim 46 from a host cell; and (b) recovering said polypeptide.

48. The isolated polypeptide of claim 46, wherein said first amino acid sequence is (b).

49. An isolated polypeptide produced by the method comprising:

(a) expressing the polypeptide of claim 48 from a host cell; and (b) recovering said polypeptide.

50. The isolated polypeptide of claim 39 further comprising a heterologous polypeptide.

51. A composition comprising the polypeptide of claim 39.

* * * * *

SEQUENCE LISTING (1) GENERAL INFORMATION:

(iii) NUMBER OF SEQUENCES:  5

(2) INFORMATION FOR SEQ ID NO:1:

(i) SEQUENCE CHARACTERISTICS:
      (A) LENGTH:  1055 BASE PAIRS
      (B) TYPE:  NUCLEIC ACID
      (C) STRANDEDNESS:  SINGLE
      (D) TOPOLOGY:  LINEAR (ii) MOLECULE TYPE:  cDNA (xi) SEQUENCE DESCRIPTION:  SEQ ID NO:1:

```
AGCCATGCAC TACCCAACTG CACTCCTCTT CCTCATCCTG GCCAATGGGA CCCAGACCTT      60

TCGCATCTGC GCCTTCAATG CCCAGCGGCT GACACTGCCC AAGGTGGCCA GGGAGCAGGT     120

GATGGACACC TTAGTTCGGA TACTGGCTCG CTGTGACATC ATGGTGCTGC AGGAGGTGGT     180

GGACTCTTCC GGCAGCGCCA TCCCGCTCCT GCTTCGAGAA CTCAATCGAT TTGATGGCTC     240

TGGGCCCTAC AGCACCCTGA GCAGCCCCCA GCTGGGGCGC AGCACCTACA TGGAGACGTA     300

TGTGTACTTC TATCGGTCAC ACAAAACACA GGTCCTGAGT TCCTACGTGT ACAACGATGA     360
```

-continued

```
GGATGACGTC TTTGCCCGGG AGCCATTTGT GGCCCAGTTC TCTTTGCCCA GCAATGTCCT    420

TCCCAGCCTG GTGTTGGTCC CGCTGCACAC CACTCCTAAG GCCGTAGAGA AGGAGCTGAA    480

CGCCCTCTAC GATGTGTTTC TGGAGGTCTC CCAGCACTGG CAGAGCAAGG ACGTGATCCT    540

GCTTGGGGAC TTCAATGCTG ACTGCGCTTC ACTGACCAAA AAGCGCCTGG ACAAGCTGGS    600

GCTGCGGACT GAGCCAGGCT TCCACTGGGT GATTGCCGAT GGGGAGGACA CCACAGTGCG    660

GGCCAGCACC CACTGCACCT ATGACCGCGT CGTGCTGCAC GGGGAGCGCT GCCGGAGTCT    720

GCTGCACACT GCGGCTGCCT TTGACTTCCC CACGAGCTTC CAGCTCACCG AGGAGGAGGC    780

CCTCAACATC AGTGACCACT ACCCCGTGGA GGTGGAGCTG AAGCTGAGCC AGGCGCACAG    840

CGTCCAGCCT CTCAGCCTCA CTGTTCTGTT GCTGCTATCA CTCCTGTCCC CTCAGCTGTG    900

CCCTGCTGCC TGAGCGTCCC CCTACCCCCC CAGGGCCTGC TGCCTTTTGG GACTTAAACC    960

CCAGCCTCCC CCGTCCATCC AGCCCTGGGG CTGGGGGGCT TCAACTATAG TTGCCCTGTG   1020

ACTGTAGTCC ACCCCTGCCT GCCTTGTTTG ATTTG                              1055
```

(2) INFORMATION FOR SEQ ID NO:2:

(i) SEQUENCE CHARACTERISTICS:
        (A) LENGTH: 351 AMINO ACIDS
        (B) TYPE: AMINO ACID
        (C) STRANDEDNESS:
        (D) TOPOLOGY: LINEAR (ii) MOLECULE TYPE: PROTEIN (xi) SEQUENCE DESCRIPTION: SEQ ID NO:2:

```
Ala Met His Tyr Pro Thr Ala Leu Leu Phe Leu Ile Leu Ala Asn
            -15                 -10                  -5

Gly Thr Gln Thr Phe Arg Ile Cys Ala Phe Asn Ala Gln Arg Leu
             1              5                  10

Thr Leu Pro Lys Val Ala Arg Glu Gln Val Met Asp Thr Leu Val
             15                 20                 25

Arg Ile Leu Ala Arg Cys Asp Ile Met Val Leu Gln Glu Val Val
             30                 35                 40

Asp Ser Ser Gly Ser Ala Ile Pro Leu Leu Leu Arg Glu Leu Asn
             45                 50                 55

Arg Phe Asp Gly Ser Gly Pro Tyr Ser Thr Leu Ser Ser Pro Gln
             60                 65                 70

Leu Gly Arg Ser Thr Tyr Met Glu Thr Tyr Val Tyr Phe Tyr Arg
             75                 80                 85

Ser His Lys Thr Gln Val Leu Ser Ser Tyr Val Tyr Asn Asp Glu
             90                 95                100

Asp Asp Val Phe Ala Arg Glu Pro Phe Val Ala Gln Phe Ser Leu
            105                110                115

Pro Ser Asn Val Leu Pro Ser Leu Val Leu Val Pro Leu His Thr
            120                125                130

Thr Pro Lys Ala Val Glu Lys Glu Leu Asn Ala Leu Tyr Asp Val
            135                140                145

Phe Leu Glu Val Ser Gln His Trp Gln Ser Lys Asp Val Ile Leu
            150                155                160

Leu Gly Asp Phe Asn Ala Asp Cys Ala Ser Leu Thr Lys Lys Arg
            165                170                175

Leu Asp Lys Leu Glu Leu Arg Thr Glu Pro Gly Phe His Trp Tyr
            180                185                190
```

```
Ile Ala Asp Gly Glu Asp Thr Thr Val Arg Ala Ser Thr His Cys
            195                 200                 205

Thr Tyr Asp Arg Val Val Leu His Gly Glu Arg Cys Arg Ser Leu
            210                 215                 220

Leu His Thr Ala Ala Ala Phe Asp Phe Pro Thr Ser Phe Gln Leu
            225                 230                 235

Thr Glu Glu Glu Ala Leu Asn Ile Ser Asp His Tyr Pro Val Glu
            240                 245                 250

Val Glu Leu Lys Leu Ser Gln Ala His Ser Val Gln Pro Leu Ser
            255                 260                 265

Leu Thr Val Leu Leu Leu Ser Leu Leu Ser Pro Gln Leu Cys
            270                 275                 280

Pro Ala Ala Xaa Ala Ser Pro Tyr Pro Pro Arg Ala Cys Cys Leu
            285                 290                 295

Leu Gly Leu Lys Pro Gln Pro Pro Ser Ile Gln Pro Trp Gly
            300                 305                 310

Trp Gly Ala Ser Thr Ile Val Ala Leu Xaa Leu Xaa Ser Thr Pro
            315                 320                 325

Ala Cys Leu Val Xaa Phe
            330
```

(2) INFORMATION FOR SEQ ID NO:3:

(i) SEQUENCE CHARACTERISTICS:
        (A) LENGTH: 27 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:3:

```
GACGCCGGAT CCCACTACCC AACTGCA                                27
```

(2) INFORMATION FOR SEQ ID NO:4:

(i) SEQUENCE CHARACTERISTICS:
        (A) LENGTH: 65 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:4:

```
GGCTGCTCTA GACAGCGTAG TCTGGCAGGT CGTATGGGTA CTTCAGCTCC ACCTCCACGG    60

GGTAG                                                               65
```

(2) INFORMATION FOR SEQ ID NO:5:

(i) SEQUENCE CHARACTERISTICS:
        (A) LENGTH: 10 AMINO ACIDS
        (B) TYPE: AMINO ACID
        (C) STRANDEDNESS:
        (D) TOPOLOGY: LINEAR (ii) MOLECULE TYPE: PROTEIN (xi) SEQUENCE DESCRIPTION: SEQ ID NO:5:

```
Met Tyr Pro Tyr Asp Val Pro Asp Tyr Ala
            5                   10
```